(12) United States Patent
McDonald et al.

(10) Patent No.: US 8,406,897 B2
(45) Date of Patent: Mar. 26, 2013

(54) SYSTEMS AND METHODS FOR DISPOSING ONE OR MORE LAYERS OF MATERIAL BETWEEN LEAD CONDUCTOR SEGMENTS OF ELECTRICAL STIMULATION SYSTEMS

(75) Inventors: Matthew Lee McDonald, Glendale, CA (US); Ross Daniel Venook, Burlingame, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 261 days.

(21) Appl. No.: 12/544,013

(22) Filed: Aug. 19, 2009

(65) Prior Publication Data

US 2011/0046706 A1 Feb. 24, 2011

(51) Int. Cl.
*A61N 1/05* (2006.01)
(52) U.S. Cl. .......... 607/116; 607/63; 600/372; 600/373; 600/377
(58) Field of Classification Search .......... 607/63, 607/115–117, 119, 121, 122; 600/372–374, 600/377, 378
See application file for complete search history.

(56) References Cited

U.S. PATENT DOCUMENTS

| | | | |
|---|---|---|---|
| 5,308,342 A * | 5/1994 | Sepetka et al. | 604/525 |
| 5,374,285 A | 12/1994 | Vaiani et al. | |
| 5,545,203 A * | 8/1996 | Doan | 607/122 |
| 5,674,272 A | 10/1997 | Bush et al. | |
| 5,869,804 A | 2/1999 | Mueller et al. | |
| 5,991,650 A | 11/1999 | Swanson et al. | |
| 6,181,969 B1 | 1/2001 | Gord | |
| 6,210,339 B1 | 4/2001 | Kiepen et al. | |
| 6,366,820 B1 | 4/2002 | Doan et al. | |
| 6,370,427 B1 | 4/2002 | Alt et al. | |
| 6,440,488 B2 | 8/2002 | Griffin, III et al. | |
| 6,505,401 B1 | 1/2003 | Doan | |
| 6,506,972 B1 * | 1/2003 | Wang | 174/36 |
| 6,516,227 B1 | 2/2003 | Meadows et al. | |

(Continued)

FOREIGN PATENT DOCUMENTS

| | | |
|---|---|---|
| WO | 0004950 A2 | 2/2000 |
| WO | 2005011806 A1 | 2/2005 |

(Continued)

OTHER PUBLICATIONS

U.S. Appl. No. 11/238,240, filed by Tom Xiaohai He on Sep. 29, 2005.

*Primary Examiner* — Carl H Layno
*Assistant Examiner* — Eugene Wu
(74) *Attorney, Agent, or Firm* — Frommer Lawrence & Haug LLP; Patrick R. Turner

(57) ABSTRACT

An implantable lead includes a lead body having a plurality of electrodes disposed on a distal end, a plurality of terminals disposed on a proximal end, and a plurality of conductors, each conductor electrically coupling at least one of the electrodes to at least one of the terminals. At least one of the conductors includes at least one unit having a multi-layer region of overlapping conductor segments. The unit including a first conductor segment extending from a beginning point to a first position, a second conductor segment extending from the first position to a second position, and a third conductor segment extending from the second position to an endpoint. The first position is between the second position and the endpoint. The second position is between the beginning point and the first position. An interlayer material is disposed between the overlapping conductor segments of the at least one multi-layer region.

20 Claims, 7 Drawing Sheets

U.S. PATENT DOCUMENTS

| | | |
|---|---|---|
| 6,609,032 B1 | 8/2003 | Woods et al. |
| 6,741,892 B1 | 5/2004 | Meadows et al. |
| 6,757,970 B1 | 7/2004 | Kuzma et al. |
| 6,795,730 B2 * | 9/2004 | Connelly et al. ............ 607/9 |
| 6,952,616 B2 | 10/2005 | Wessman et al. |
| 7,039,470 B1 | 5/2006 | Wessman |
| 7,047,081 B2 | 5/2006 | Kuzma |
| 7,047,627 B2 | 5/2006 | Black et al. |
| 7,149,585 B2 * | 12/2006 | Wessman et al. .......... 607/116 |
| 7,236,834 B2 | 6/2007 | Christopherson et al. |
| 2003/0114905 A1 | 6/2003 | Kuzma |
| 2004/0059392 A1 | 3/2004 | Parramon et al. |
| 2004/0199069 A1 * | 10/2004 | Connelly et al. .......... 600/412 |
| 2004/0210289 A1 * | 10/2004 | Wang et al. ............... 607/116 |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0070982 A1 | 3/2005 | Heruth et al. |
| 2005/0113899 A1 | 5/2005 | Cross |
| 2005/0137670 A1 | 6/2005 | Christopherson et al. |
| 2005/0165465 A1 | 7/2005 | Pianca et al. |
| 2007/0027514 A1 | 2/2007 | Gerber |
| 2007/0027515 A1 | 2/2007 | Gerber |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0219595 A1 | 9/2007 | He |
| 2007/0239243 A1 | 10/2007 | Moffitt et al. |
| 2007/0299490 A1 | 12/2007 | Yang et al. |
| 2008/0033497 A1 | 2/2008 | Bulkes et al. |
| 2008/0243218 A1 | 10/2008 | Bottomley et al. |
| 2008/0262584 A1 | 10/2008 | Bottomley et al. |
| 2008/0269856 A1 | 10/2008 | Cross et al. |
| 2008/0269857 A1 | 10/2008 | Cross et al. |
| 2008/0269858 A1 | 10/2008 | Cross et al. |

FOREIGN PATENT DOCUMENTS

| | | |
|---|---|---|
| WO | 2005011807 A1 | 2/2005 |
| WO | 2005032654 A1 | 4/2005 |
| WO | 2007127997 A2 | 11/2007 |
| WO | 2007127998 A2 | 11/2007 |
| WO | 2007133930 A2 | 11/2007 |
| WO | 2008036865 A2 | 3/2008 |
| WO | 2008051913 A1 | 5/2008 |
| WO | 2008115383 A2 | 9/2008 |
| WO | 2008115426 A1 | 9/2008 |

* cited by examiner

US 8,406,897 B2

SYSTEMS AND METHODS FOR DISPOSING ONE OR MORE LAYERS OF MATERIAL BETWEEN LEAD CONDUCTOR SEGMENTS OF ELECTRICAL STIMULATION SYSTEMS

FIELD

The present invention is directed to the area of implantable electrical stimulation systems and methods of making and using the systems. The present invention is also directed to implantable electrical stimulation leads having interlayer material disposed between overlapping conductor segments of the leads, as well as methods of making and using the conductors, leads, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable lead includes a lead body having a distal end, a proximal end, and a longitudinal length. The lead body also includes a plurality of electrodes disposed on the distal end of the lead body, a plurality of terminals disposed on the proximal end of the lead body, and a plurality of conductors. Each conductor electrically couples at least one of the electrodes to at least one of the terminals. At least one of the conductors includes at least one unit having a multi-layer region of overlapping conductor segments. The at least one unit includes a first conductor segment extending along the lead body from a beginning point to a first position, a second conductor segment extending along the lead body from the first position to a second position, and a third conductor segment extending along the lead body from the second position to an endpoint. The first position is between the second position and the endpoint. The second position is between the beginning point and the first position. An interlayer material is disposed between the overlapping conductor segments of the at least one multi-layer region.

In another embodiment, an electrical stimulating system includes a lead, a control module, and a connector for receiving the lead. The lead includes a lead body having a distal end, a proximal end, and a longitudinal length. The lead body also includes a plurality of electrodes disposed on the distal end of the lead body, a plurality of terminals disposed on the proximal end of the lead body, and a plurality of conductors. Each conductor electrically couples at least one of the electrodes to at least one of the terminals. At least one of the conductors includes at least one unit having a multi-layer region of overlapping conductor segments. The at least one unit includes a first conductor segment extending along the lead body from a beginning point to a first position, a second conductor segment extending along the lead body from the first position to a second position, and a third conductor segment extending along the lead body from the second position to an endpoint. The first position is between the second position and the endpoint. The second position is between the beginning point and the first position. An interlayer material is disposed between the overlapping conductor segments of the at least one multi-layer region. The control module is configured and arranged to electrically couple to the proximal end of the lead. The control module includes a housing and an electronic subassembly disposed in the housing. The connector has a proximal end, a distal end, and a longitudinal length. The connector includes a connector housing that defines a port at the distal end of the connector. The port is configured and arranged for receiving the proximal end of the lead. A plurality of connector contacts are disposed in the connector housing. The connector contacts are configured and arranged to couple to at least one of the plurality of terminals disposed on the proximal end of the lead.

In yet another embodiment, a method for forming an implantable lead includes coiling a plurality of elongated conductors arranged in a single layer in a first direction from a beginning point to a first position to form a first conductor segment. A first layer of interlayer material is disposed over at least a portion of the first conductor segment. The plurality of elongated conductors are coiled over the first layer of interlayer material in a second direction that is opposite to the first direction from the first position to a second position to form a second conductor segment. A second layer of interlayer material is disposed over at least a portion of the second conductor segment. The plurality of elongated conductors are coiled over the second layer of interlayer material in the first direction from the second position to an endpoint to form a third conductor segment. A first end of each of the plurality of elongated conductors is coupled to an electrode. A second end of each of the plurality of elongated conductors is coupled to a terminal.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having interlayer material disposed between overlapping conductor segments of the leads, as well as methods of making and using the conductors, leads, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741, 892; and U.S. patent application Ser. Nos. 10/353,101, 10/503,281, 11/238,240; 11/319,291; 11/327,880; 11/375, 638; 11/393,991; and 11/396,309, all of which are incorporated by reference.

Figure 1:
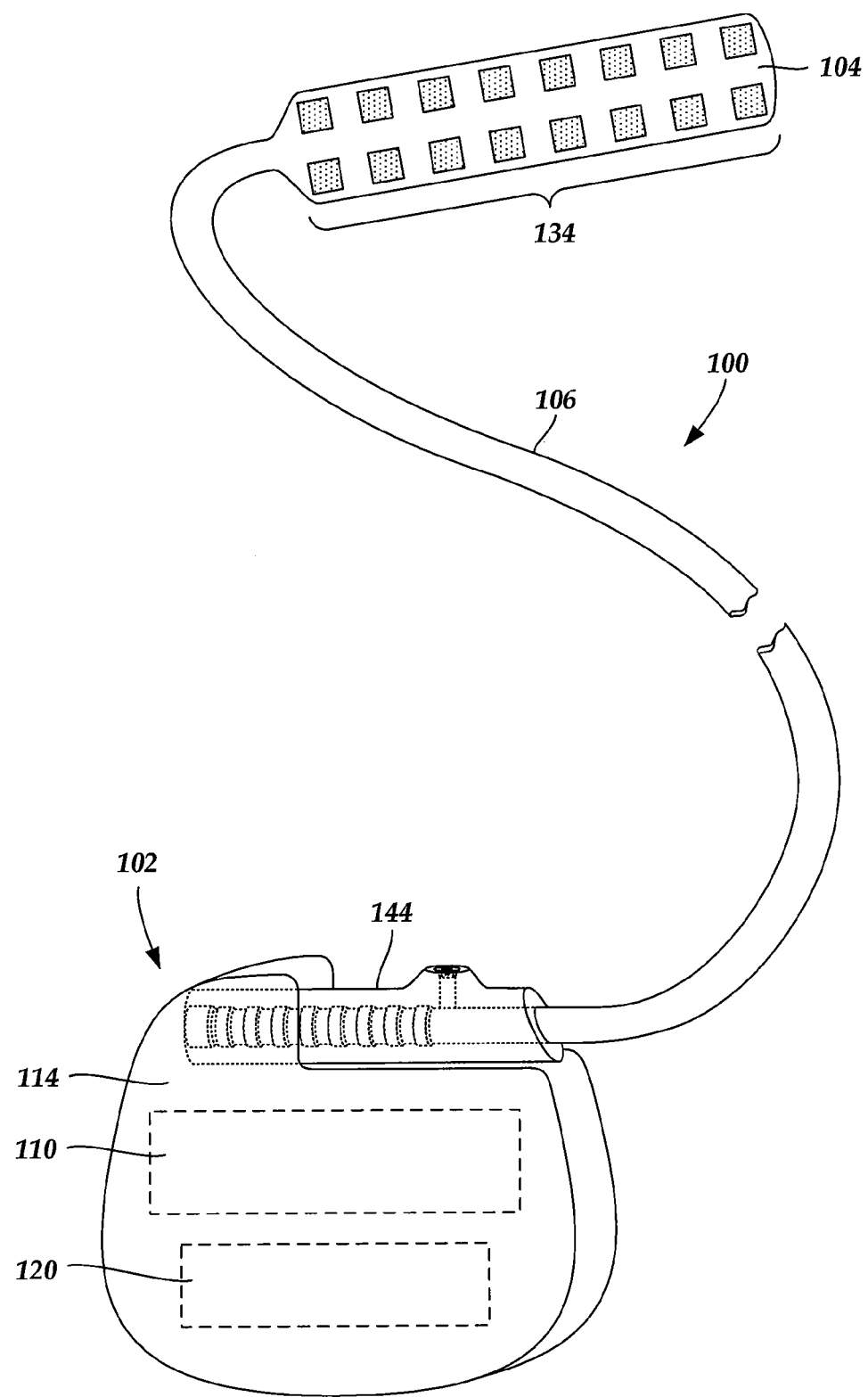
FIG. 1 is a schematic view of one embodiment of an electrical stimulation system, according to the invention.
Figure 2:
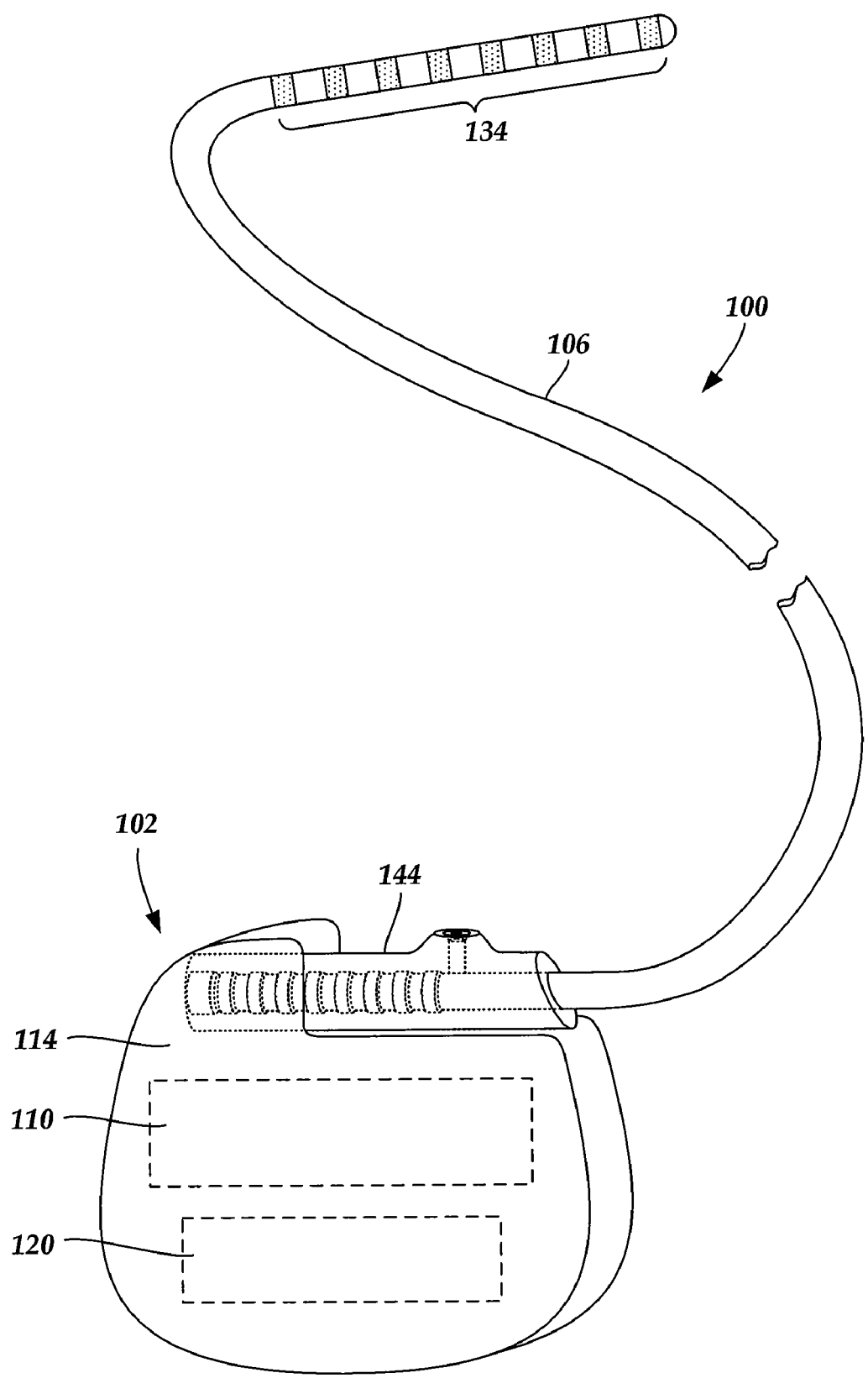
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIG. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 324 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
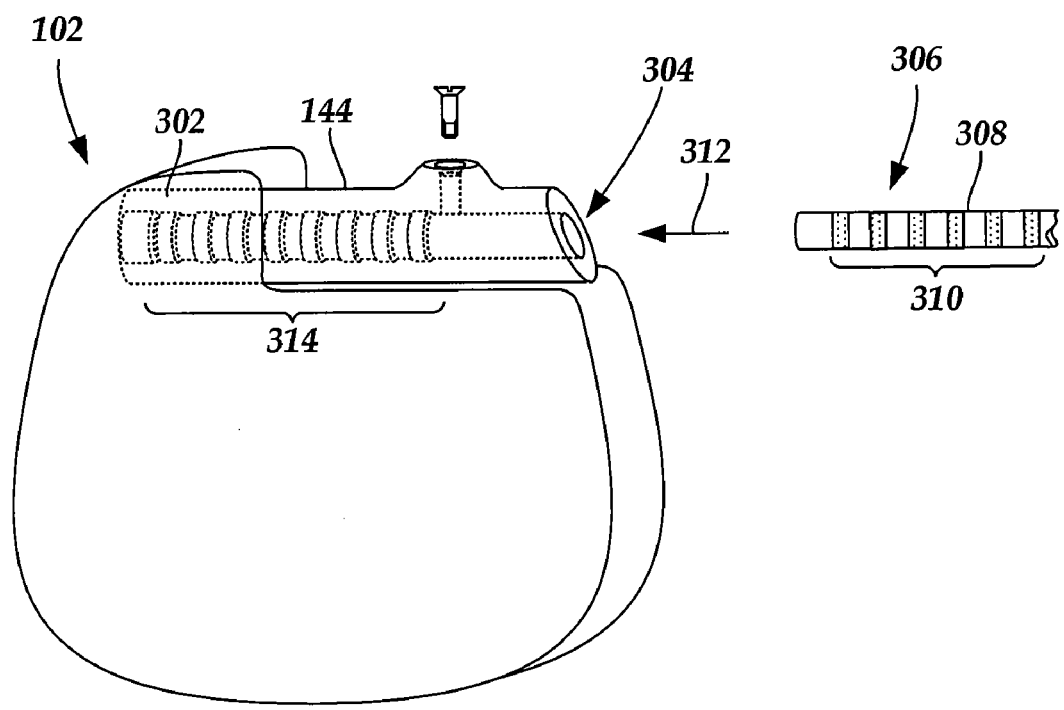
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
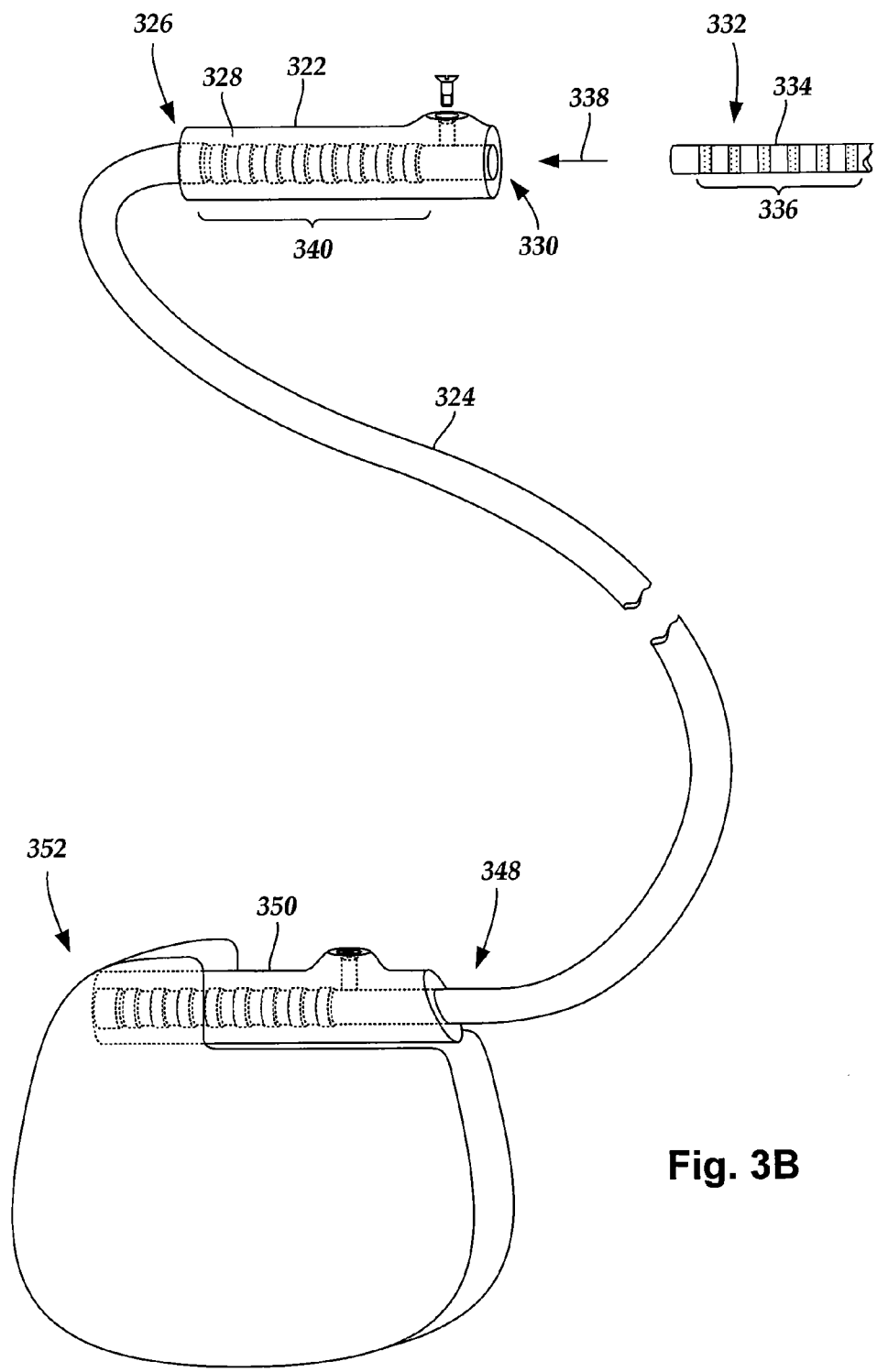
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting at least one terminal to an electrode (or other conductive contact) can be arranged in a conductor path to eliminate or reduce the effect of RF irradiation, such as that generated during magnetic resonance imaging ("MRI"). The conductor path includes a plurality of units arranged in series. In some embodiments, the units are disposed along a single continuous conductor. In other embodiments, the units are separate conductive elements electrically coupled together.

Each unit includes at least three conductor segments that at least partially overlap one another to form a multi-layer region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-layer region flanking at least one end of the multi-layer region.

The units may be electrically continuous such that the endpoint of a first unit is the beginning point of the next consecutive unit. At least one of the beginning points may be a terminal or an electrode (or other conductive contact). Likewise, at least one of the endpoints may be a terminal or an electrode (or other conductive contact). In preferred embodiments, the conductor segments are each coiled. In at least some embodiments, the conductor segments are coiled around a conductor placement sleeve. In at least some embodiments, the conductor placement sleeve defines a lumen that optionally is configured and arranged to receive a stiffening member (e.g., a stylet, or the like).

In at least some embodiments, at least one of the first, second, or third conductor segments is substantially straight. In at least some embodiments, the first and third conductor segments are substantially straight and the second conductor segment is coiled. In at least some other embodiments, all three conductor segments are substantially straight. It will be understood that the term "substantially straight conductor segment" means that the conductor segment is not coiled. A "substantially straight conductor segment" may be curved, particularly when the lead itself is curved (see, for example, FIG. 1).

In at least some embodiments, the conductor segments are all formed from the same length of conductive material (e.g., wire or the like). The conductors may have a single filament or be multi-filar. In preferred embodiments, the conductors are multi-filar. In at least some embodiments, two or more of the conductor segments can be individual pieces of conductive material that are electrically coupled (e.g., soldered or welded) together. In at least some embodiments, a layer of insulation ("conductor insulation") is disposed over each of the conductor segments.

In at least some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of the layer of conductor insulation is different for the different segments.

Figure 4:
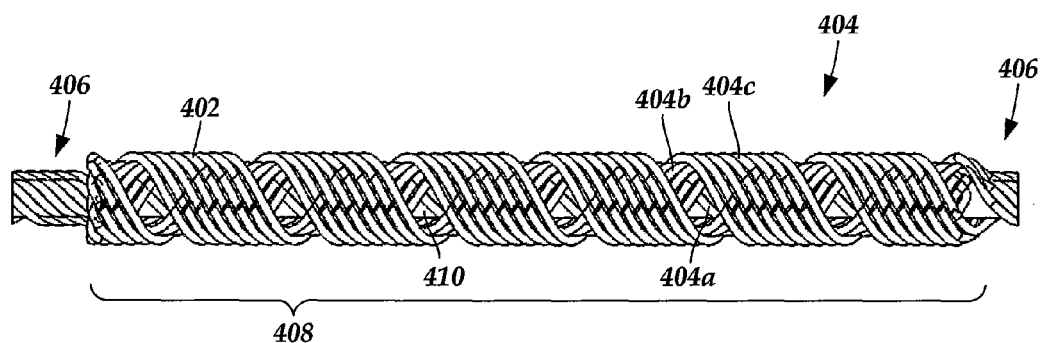
FIG. 4 is a schematic side view of one embodiment of portions of a plurality of conductors configured into a multi-layer region of overlapping conductor segments, according to the invention.

FIG. 4 schematically illustrates one embodiment of a plurality of conductors 402. The conductors 402 are configured into a plurality of units, such as unit 404. Each unit includes a first conductor segment 404a, a second conductor segment 404b, and a third conductor segment 404c. In at least some embodiments, conductor insulation is disposed over the conductors 402 to electrically isolate each of the conductors 402 from one another.

Any suitable number of units may be disposed along the length of the lead including, for example, one, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along the length of the lead, the plurality of units form a repeating series of single-layer regions, such as the single-layer regions 406, separated from one another by a multi-layer region, such as the multi-layer region 408.

In at least some embodiments, the conductors 402 are disposed along a conductor placement sleeve 410. The conductor placement sleeve 410 can be formed from any suitable biocompatible material including, for example, one or more polymers. Conductor insulation is typically disposed over the conductors 402 to encapsulate the conductors 402 and electrically isolate the conductors 402 from one another.

In at least some embodiments, one or more units may be disposed in an elongated member (e.g., a lead or lead extension). The ends of the conductors 402 are coupled to terminals, electrodes, or conductive contacts. In preferred embodiments, each of the conductors in an elongated member is provided in one or more units. In at least some embodiments, only a subset of the conductors disposed in an elongated member are provided in one or more units, the remaining conductors having a different arrangement (for example, a single straight or coiled conductor segment between the terminal(s) and electrode(s)/conductive contact(s)).

Implanted conductors within elongated members (e.g., leads, lead extensions, or the like) may be subjected to many different physical stresses. For example, patient movement may cause conductors to become deformed (e.g., bent, squeezed, stretched, or the like). As a result, the overlapping conductor segments of the multi-layer regions within the units may rub against each other, potentially causing conductor insulation disposed over the conductors to degrade. Physical stresses may also cause multi-layer regions to uncoil or move relative to one another, thereby reducing, or even eliminating, the protection against undesired heating, induced currents, or premature mechanical failure. Implanted conductors may also become exposed to bodily fluids seeping into spaces between conductor segments. Bodily fluids may cause damage to the conductors, as well. For example, bodily fluids may cause degradation of conductor insulation, short-circuiting of the conductors, or the like.

Figure 5A:
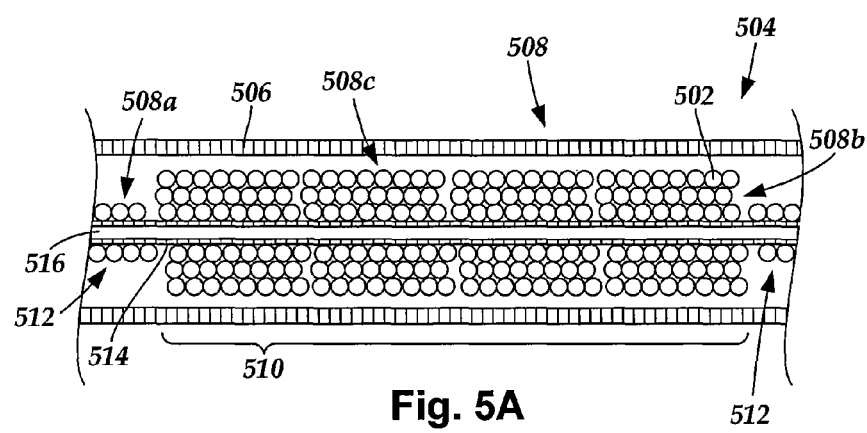
FIG. 5A is a schematic longitudinal cross-sectional view of one embodiment of portions of a plurality of conductors configured into a multi-layer region of overlapping conductor segments and disposed in an elongated member, according to the invention.

In at least some embodiments, interlayer material is disposed between conductor segments of multi-layer regions of conductors to reduce rubbing between conductor segments. In at least some embodiments, the interlayer material is disposed between overlapping conductor segments. FIG. 5A is a schematic longitudinal cross-sectional view of one embodiment of portions of a plurality of conductors 502 disposed in an elongated member 504 having a body 506. The illustrated portions of the conductors 502 includes a unit 508 having a multi-layer region 510. In at least some embodiments, the conductors 502 may include a plurality of units coupled serially to form a repeating series of multi-layer regions, such as the multi-layer region 510, separated from one another by single-layer regions 512.

The unit 508 includes a first conductor segment 508a, a second conductor segment 508b, and a third conductor segment 508c. In at least some embodiments, the conductors 502 are disposed over a conductor placement sleeve 514. In at least some embodiments, the conductor placement sleeve 514 defines a lumen 516. In at least some embodiments, the lumen 516 is configured and arranged to receive a stiffening member (e.g., a stylet, or the like) for facilitating guidance of the conductors 502 (e.g., to a target stimulation site within a patient). In at least some embodiments, one or more layers of lining material (not shown) may be disposed between the conductor placement sleeve 514 and the conductors 502.

Figure 5B:
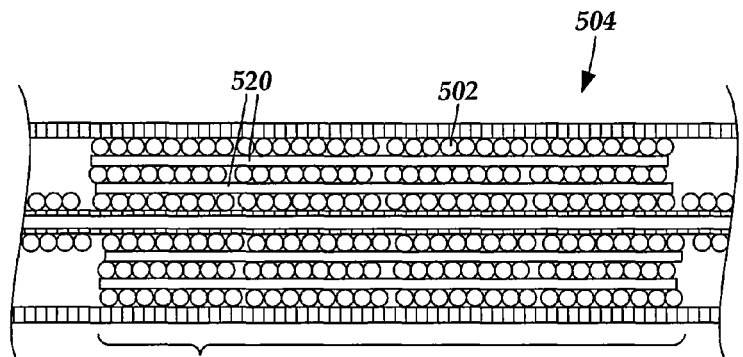
FIG. 5B is a schematic longitudinal cross-sectional view of one embodiment of interlayer material disposed between overlapping conductor segments of the multi-layer region of FIG. 5A, according to the invention.

FIG. 5B is a schematic longitudinal cross-sectional view of one embodiment of portions of the conductors 502 disposed in the elongated member 504. Interlayer material 520 is disposed between overlapping conductor segments of the multi-layer region 510. In at least some embodiments, the interlayer material 520 may be disposed between the conductor placement sleeve 514 and the one or more multi-layer regions, such as the multi-layer region 510, as well as one or more single-layer regions, such as the single-layer regions 512, as shown in FIG. 5C.

The interlayer material 520 may be formed from any biocompatible material(s) suitable for implantation including, for example, one or more thermoplastic polymers (e.g., polyurethane, fluoropolymers, or the like), one or more thermoset polymers (e.g., silicone, or the like), conductive filler material, or the like or combinations thereof.

Figure 5C:
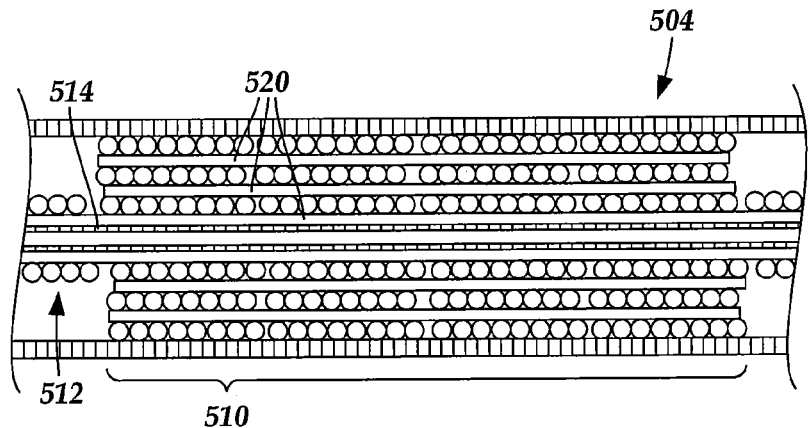
FIG. 5C is a schematic longitudinal cross-sectional view of one embodiment of interlayer material disposed between overlapping conductor segments of the multi-layer region of FIG. 5A and also between conductor segments and a conductor placement sleeve, according to the invention.

As shown in FIGS. 5B and 5C, the interlayer material 520 may fill open spaces between the overlapping conductor segments of multi-layer regions. In at least some embodiments, the interlayer material 520 may fill open spaces between conductors of the same conductor segment. In at least some embodiments, the interlayer material 520 mitigates degradation of conductor insulation due to rubbing between layers of a multi-layer region. In at least some embodiments, the interlayer material 520 functions as an adhesive to prevent uncoiling of multi-layer regions and to maintain multi-layer regions in position relative to one another. In at least some embodiments, the interlayer material 520 reduces, modulates, or even eliminates, seepage of bodily fluids between the conductor segments of the multi-layer regions.

In at least some embodiments, the interlayer material 520 facilitates radial spacing between conductor segments of a multi-layer region (i.e., the interlayer material 520 provides radial separation between adjacent layers of conductor segments of the multi-layer region). In at least some embodiments, the interlayer material 520 facilitates maintaining constant axial spacing between adjacent multi-layer regions (i.e., the interlayer material 520 reduces the likelihood of the multi-layer regions uncoiling, or partially uncoiling, thereby maintaining axial spacing between neighboring units). In at least some embodiments, the interlayer material 520 facilitates controlling the pitch of coiled conductors within multi-layer regions (i.e., the interlayer material 520 reduces the likelihood of the multi-layer regions uncoiling, or partially uncoiling, thereby affecting the pitch of the coiled conductors). In at least some embodiments, the interlayer material 520 facilitates controlling the pitch of coiled conductors within single-layer regions (i.e., the interlayer material 520 reduces the likelihood of the single-layer regions uncoiling, or partially uncoiling, thereby affecting the pitch of the coiled conductors).

It will be understood that, in at least some embodiments, the interlayer material 520 is formed from a plurality of materials. In at least some embodiments, the one or more materials used to form the interlayer material 520 may include variations of the same material. For example, one or more substances may be added to a given material under different conditions (e.g., temperature, pressure, or the like) or in different amounts, to change one or more characteristics of the material, such as melting point, durability, rigidity, conductivity, viscosity, flexibility, or the like or combinations thereof.

As an example, polymers of different durometers may be used to vary the stiffness of the interlayer material 520. For example, both 55D- and 7D-hardness polyurethanes may be used. These polyurethanes differ in the number of hard and soft blocks in the polymer. In another example, two similar materials (e.g., silicone or polyurethane) may differ due to differences in characteristics such as degree of cross-linking or different molecular weight.

In at least some embodiments, the interlayer material 520 is formed from a material that is flowable upon application. In at least some embodiments, the interlayer material 520 is formed from at least one material that may set or cross-link after flowing, for example, as temperature is lowered or when irradiated with light (e.g., visible, ultraviolet, or infrared) or when heated to a cross-linking activation temperature. In at least some embodiments, the interlayer material 520 is formed from a doped material, or a composite material (e.g., a material filled with glass, carbon fiber, or the like). In at least some embodiments, the interlayer material 520 is a foam. In at least some embodiments, the interlayer material 520 is configured and arranged to couple (e.g., adhere, coat, wick, or the like) with one or more of the conductor placement sleeve 514, electrodes (see e.g., 134 of FIG. 1), terminals (see e.g., 310 of FIG. 3A), or conductive contacts (see e.g., 340 of FIG. 3B). In at least some embodiments, at least one of the materials used to form the interlayer material 520 varies along the length of the conductors 502.

It will additionally be understood that the interlayer material 520 may, by itself, or by the inclusion one or more additives combined with the one or more materials of the interlayer material 520, affect one or more mechanical properties, or characteristics, of the elongated member 504 including, for example, durability, rigidity, conductivity, viscosity, flexibility, or the like or combinations thereof. For example, one or more filaments may be impregnated in the interlayer material 520. In at least some embodiments, polyethylene terephthalate may be added to the interlayer material 520 to alter one or more of the above-mentioned properties. In at least some embodiments, one or more conductive polymers, such as poly(3,4-ethylenedioxythiophene), could also be added to the interlayer material 520 in varying amounts to affect conductivity.

In at least some embodiments, the interlayer material 520 is more flexible than the conductors 502. In at least some embodiments, the interlayer material 520 is more flexible than the conductor placement sleeve 514. In at least some embodiments, the flexibility of an elongated member 504 may be adjusted by varying the flexibility of the interlayer material 520. In at least some embodiments, the combination of materials used to form interlayer material 520 improves the flex fatigue properties of the elongated member 504. In other words, in at least some embodiments, the combination of materials used to form the interlayer material 520 may reduce the forces transmitted to the conductors 502, as compared to conductors configured into units that do not include the interlayer material 520.

In at least some embodiments, the interlayer material 520 (or one or more additives added to the interlayer material 520) effects one or more electromagnetic properties of the elongated member 504. For example, the interlayer material 520 may alter one or more of the conductance, inductance, capacitance, or the like, of the elongated member 504. In at least some embodiments, one or more of the conductance, inductance, or capacitance properties are only altered when exposed to RF energy within certain frequency ranges. For example, in at least some embodiments, one or more of the conductance, inductance, or capacitance properties are only altered when exposed to frequency ranges at or around frequencies used during MRI procedures (e.g., 64 MHz, 128 MHz, or the like). In at least some embodiments, the interlayer material 520 can be made lossy, such as by inclusion of conductive elements, thereby lowering resonant behavior of currents flowing in one or more of the conductors 502. In at least some embodiments, the interlayer material 520 is configured and arranged to alter one or more of the capacitance or the inductance of the elongated member to provide increased electromagnetic stability of the elongated member under one or more implanted conditions (e.g., at body temperature, at body pressure, while being soaked in bodily fluids, or the like or combinations thereof).

The interlayer material 520 may be disposed between overlapping conductor segments of a multi-layer region in many different ways. In at least some embodiments, at least one of the interlayer materials 520 is a flowable material that penetrates and fills in open spaces between overlapping layers of conductor segments during formation of the multi-layer region. In at least some embodiments, the interlayer material 520 is molded in place over the conductor segments during formation of the multi-layer region. In at least some embodiments, the interlayer material 520 is sprayed on conductor segments during formation of the multi-layer region. In at least some embodiments, the interlayer material 520 is dip molded onto conductor segments during formation of the multi-layer region.

In at least some embodiments, the interlayer material 520 includes a tubing with a slit formed along its length and disposed over the conductor segments of the multi-layer region as the conductor segments are fabricated. Once the tubing is disposed over the conductor segments, one or more additional layers of conductor segments can be disposed over the tubing to hold the tubing in place.

Figure 6A:
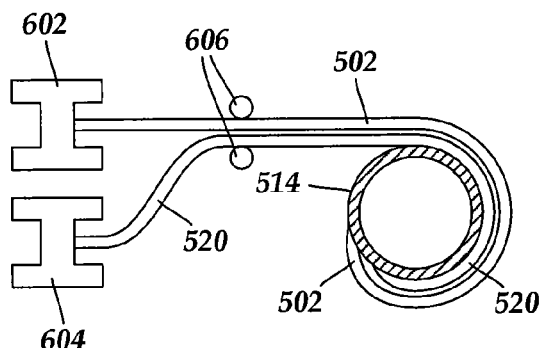
FIG. 6A is a schematic cross-sectional view of one embodiment of conductors and interlayer material being applied to a conductor placement sleeve, according to the inventions.
Figure 6B:
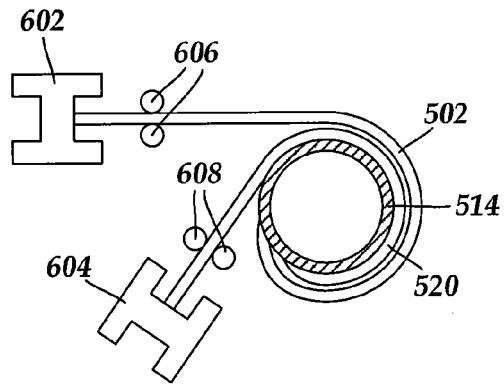
FIG. 6B is a schematic cross-sectional view of another embodiment of conductors and interlayer material being applied to a conductor placement sleeve, according to the inventions.

As discussed above, in preferred embodiments, the conductor units include coiled conductors. In at least some embodiments, the interlayer material 520 is disposed between conductor segments as part of a conductor coiling process. For example, FIG. 6A is a schematic cross-sectional view of one embodiment of the conductors 502 and the interlayer material 520 being applied to the conductor placement sleeve 514. In FIG. 6A, the conductors 502 and the interlayer material 520 are both being unwound from spools 602 and 604, respectively, and coiled over the conductor placement sleeve 514. In FIG. 6A, the conductors 502 and the interlayer material 520 are both shown passing through the same winding head 606 during the coiling process. In at least some embodiments, the conductors 502 and the interlayer material 520 are passed through separate winding heads 606 and 608, respectively, as shown in FIG. 6B.

In at least some embodiments, the interlayer material 520 can be processed after the interlayer material 520 has been applied between conductor segments of the multi-layer region 510. For example, in at least some embodiments, the interlayer material 520 is reflowed using heat to at least partially melt one or more materials of the interlayer material 520. In at least some embodiments, at least a portion of the interlayer material 520 is soaked in a solution (e.g., a saline solution, or the like) that causes the interlayer material 520 to uptake one or more materials. In at least some embodiments, the one or more materials that are taken up by the interlayer material 520 can affect one or more of the physical or electromagnetic properties of the interlayer material 520.

Figure 7:
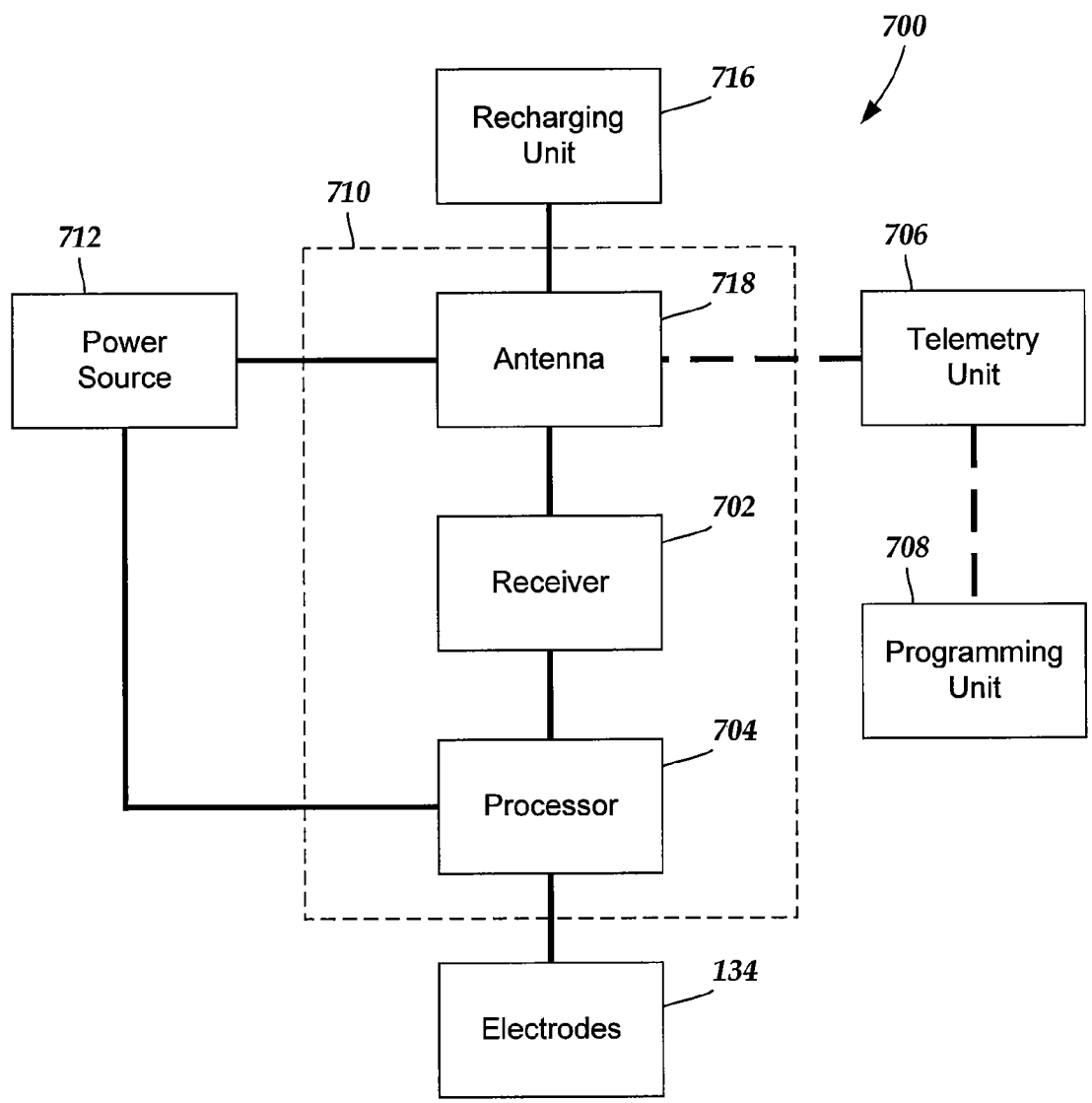
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead comprising:
 a lead body having a distal end, a proximal end, and a longitudinal length;
 a plurality of electrodes disposed along the distal end of the lead body;
 a plurality of terminals disposed along the proximal end of the lead body;
 a plurality of conductors, each conductor electrically coupling at least one of the electrodes to at least one of the terminals, wherein at least one of the plurality of conductors comprises a first conductor that is arranged into at least one unit, the at least one unit comprising
  a first conductor segment of the first conductor extending along the lead body from beginning point to a first position,
  a second conductor segment of the first conductor extending along the lead body from the first position to a second position, and
  a third conductor segment of the first conductor extending along the lead body from the second position to an endpoint, wherein the first position is between the second position and the endpoint, and the second position is between the beginning point and the first position,
wherein units are arranged so as to form a plurality of single-layer regions and a plurality of multi-layer regions, wherein the multi-layer regions are each formed from at least two overlapping conductor segments selected from the first, second, and third conductor segments of the first conductor,
wherein the plurality of single-layer regions and the plurality of multi-layer regions are arranged along the longitudinal length of the lead body in an axially-alternating configuration with each individual single-layer region of the plurality of single-layer regions abutted by at least one of the plurality of multi-layer regions;
wherein the plurality of multi-layer regions comprises a first multi-layer region and a second multi-layer region, and wherein the plurality of single-layer regions comprises a first single-layer region that is disposed between the first multi-layer region and the second multi-layer region and that abuts both the first multi-layer region and second multi-layer region;
a plurality of discontinuous, axially-spaced-apart sections of interlayer material disposed along the longitudinal length of the lead body, wherein the interlayer material is disposed between at least two of the overlapping conductor segments of each of the first multi-layer region and the second multi-layer region, wherein the interlayer material completely physically separates the at least two overlapping conductor segments from each other, wherein the interlayer material is configured and arranged to prevent uncoiling of each of the first and second multi-layer regions and to maintain a constant axial spacing between the first multi-layer region and the second multi-layer region, and wherein the interlayer material comprises at least one of a doped material or foam; and
a conductor insulation disposed over at least a portion of at least one of the plurality of conductors, the conductor insulation disposed between the at least one conductor and the interlayer material.

2. The lead of claim 1, further comprising a conductor placement sleeve disposed in the lead body and extending along at least a portion of the lead body, wherein the plurality of conductors are disposed over the conductor placement sleeve.

3. The lead of claim 2, wherein the interlayer material is a first interlayer material, and wherein the lead further comprises a second interlayer material disposed between the conductor placement sleeve and at least one of the conductor segments of at least one of the plurality of multi-layer regions, the second interlayer material completely physically separating the at least one conductor segment from the conductor placement sleeve.

4. The lead of claim 3, wherein the second interlayer material is disposed between the conductor placement sleeve and at least one non-overlapping conductor segment of at least one of the plurality of single-layer regions, the second interlayer material completely physically separating the at least one non-overlapping conductor segment from the conductor placement sleeve.

5. The lead of claim 1, wherein the interlayer material is configured and arranged to alter at least one of capacitance or inductance of the lead.

6. The lead of claim 1, wherein the interlayer material is formed from a flowable material that is configured and arranged to set or cross-link when cooled after flowing.

7. The lead of claim 1, wherein the interlayer material is more flexible than at least one of the plurality of conductors.

8. The lead of claim 1, wherein the interlayer material comprises glass.

9. The lead of claim 1, wherein the interlayer material is doped with a material configured and arranged to increase the lossiness of the lead.

10. The lead of claim 1, wherein the interlayer material comprises at least one conductive polymer.

11. The lead of claim 1, wherein the interlayer material comprises polyethylene terephthalate.

12. The lead of claim 1, wherein the interlayer material is disposed between the first conductor segment and the second conductor segment of at least one of the first multi-layer region or the second multi-layer region.

13. The lead of claim 1, wherein the interlayer material is disposed between the second conductor segment and the third conductor segment of at least one of the first multi-layer region or the second multi-layer region.

14. The lead of claim 1, wherein the interlayer material is disposed solely between overlapping conductor segments of the plurality of multi-layer regions.

15. The lead of claim 1, wherein each of the conductor segments is coiled.

16. An electrical stimulating system comprising:
the implantable lead of claim 1;
a control module configured and arranged to electrically couple to the proximal end of the lead, the control module comprising
a housing, and
an electronic subassembly disposed in the housing; and
a connector for receiving the lead, the connector having a proximal end, a distal end, and a longitudinal length, the connector comprising
a connector housing defining a port at the distal end of the connector, the port configured and arranged for receiving the proximal end of the lead, and
a plurality of connector contacts disposed in the connector housing, the connector contacts configured and arranged to couple to at least one of the plurality of terminals disposed on the proximal end of the lead.

17. The electrical stimulating system of claim 16, further comprising a lead extension having a proximal end and a distal end, the connector disposed on the distal end of the lead extension.

18. The electrical stimulating system of claim 17, wherein the lead extension has a distal end, a proximal end, and a longitudinal length, the lead extension comprising
a plurality of conductive contacts disposed on the distal end of the lead extension;
a plurality of terminals disposed on the proximal end of the lead extension; and
a plurality of conductors, each conductor electrically coupling at least one of the electrodes to at least one of the terminals, wherein at least one of the conductors comprises at least one unit comprising a multi-layer region of overlapping conductor segments, the at least one unit comprising
a first conductor segment extending along the lead extension from a beginning point to a first position,
a second conductor segment extending along the lead extension from the first position to a second position,
a third conductor segment extending along the lead extension from the second position to an endpoint, wherein the first position is between the second position and the endpoint, and the second position is between the beginning point and the first position, wherein the overlapping conductor segments of the multi-layer region comprise a first conductor segment and a second conductor segment disposed concentrically over the first conductor segment, and an interlayer material disposed between the first conductor segment and the second conductor segment, the interlayer material completely physically separating the first conductor segment from the second conductor segment.

19. The electrical stimulating system of claim 17, wherein the proximal end of the lead extension is configured and arranged for insertion into another connector.

20. The electrical stimulating system of claim 16, wherein the connector is disposed on the control module.

* * * * *